United States Patent
Calle et al.

(10) Patent No.: US 8,583,244 B1
(45) Date of Patent: Nov. 12, 2013

(54) METHODS AND SYSTEMS FOR SELECTIVELY PERFORMING A QUICK INITIALIZATION OF A SOUND PROCESSOR

(75) Inventors: Guillermo A. Calle, Moorpark, CA (US); Kevin Hood, Coquitlam (CA)

(73) Assignee: Advanced Bionics AG, Zug (CH)

( * ) Notice: Subject to any disclaimer, the term of this patent is extended or adjusted under 35 U.S.C. 154(b) by 770 days.

(21) Appl. No.: 12/847,102

(22) Filed: Jul. 30, 2010

(51) Int. Cl.
*A61N 1/36* (2006.01)
(52) U.S. Cl.
USPC .............................. 607/55; 607/137
(58) Field of Classification Search
USPC ............................ 607/55–57, 137
See application file for complete search history.

(56) References Cited

U.S. PATENT DOCUMENTS 6,826,430 B2 * 11/2004 Faltys et al. ............. 607/137
7,801,616 B2 * 9/2010 De Paep ................. 607/57

* cited by examiner

*Primary Examiner* — Brian T Gedeon
(74) *Attorney, Agent, or Firm* — ALG Intellectual Property, LLC

(57) ABSTRACT

An exemplary method of initializing a sound processor includes detecting a condition prompting an initialization of a sound processor for a cochlear implant patient, verifying, in response to the detecting, an integrity of program data stored by the sound processor, and performing, in response to the verifying, a quick initialization of the sound processor by selectively rewriting header information stored by the sound processor to associate the sound processor with the patient without rewriting the program data stored by the sound processor. Corresponding methods and systems are also described.

20 Claims, 9 Drawing Sheets

METHODS AND SYSTEMS FOR SELECTIVELY PERFORMING A QUICK INITIALIZATION OF A SOUND PROCESSOR

BACKGROUND INFORMATION

The natural sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers by way of one or more channels formed by an array of electrodes implanted in the cochlea. Direct stimulation of the auditory nerve fibers leads to the perception of sound in the brain and at least partial restoration of hearing function.

When a cochlear implant system is initially implanted in a patient, and during follow-up tests and checkups thereafter, it is usually necessary to fit the cochlear implant system to the patient. Fitting of a cochlear implant system to a patient is typically performed by an audiologist or the like who presents various stimuli to the patient and relies on subjective feedback from the patient as to how such stimuli are perceived.

Before a cochlear implant system may be fitted to a patient, a sound processor included in the cochlear implant system often has to be initialized or prepared for use by the particular patient. During the initialization process, data stored within the sound processor is often deleted and rewritten with data specific to the patient. This process can be frustratingly slow and tedious for audiologists and cochlear implant patients alike.

SUMMARY

An exemplary method of initializing a sound processor includes detecting a condition prompting an initialization of a sound processor for a cochlear implant patient, verifying, in response to the detecting, an integrity of program data stored by the sound processor, and performing, in response to the verifying, a quick initialization of the sound processor by selectively rewriting header information stored by the sound processor to associate the sound processor with the patient without rewriting the program data stored by the sound processor.

Another exemplary method of initializing a sound processor includes detecting a condition prompting an initialization of a sound processor for a cochlear implant patient, determining, in response to the detecting, whether program data stored by the sound processor and representative of one or more sound processing programs is valid and up-to-date, performing a quick initialization of the sound processor if the program data is valid and up-to-date, and performing a full initialization of the sound processor if the program data is not valid or up-to-date.

An exemplary system for initializing a sound processor includes a fitting facility that detects a condition prompting an initialization of a sound processor for a cochlear implant patient, a data analysis facility communicatively coupled to the fitting facility and that verifies an integrity of program data stored by the sound processor in response to the detection of the condition, and an initialization facility communicatively coupled to the data analysis facility and configured to perform a quick initialization of the sound processor in response to the verification of the integrity of the program data by selectively rewriting header information stored by the sound processor to associate the sound processor with the patient without rewriting the program data stored by the sound processor.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Methods and systems for initializing a sound processor are described herein. As described in more detail below, a fitting subsystem may be configured to detect a condition prompting an initialization of a sound processor for a cochlear implant patient. The fitting subsystem may determine whether program data stored by the sound processor and representative of one or more sound processing programs is valid and up-to-date. If the fitting subsystem determines that the program data is valid and up-to-date, the fitting subsystem may perform a quick initialization of the sound processor. Alternatively, if the fitting subsystem determines that the program data is not valid or up-to-date, the fitting subsystem may perform a full initialization of the sound processor. Exemplary steps that may be included in a quick initialization and a full initialization of a sound processor will be described in more detail below.

Numerous advantages may be associated with the methods and systems described herein. For example, by selectively performing a quick initialization of a sound processor instead of a full initialization, a fitting subsystem (e.g., a fitting station utilized by an audiologist) may prepare the sound processor to be fitted to a particular cochlear implant patient in a relatively more efficient and rapid manner. In this manner, a sound processor may be more effectively fitted to a patient.

Figure 1:
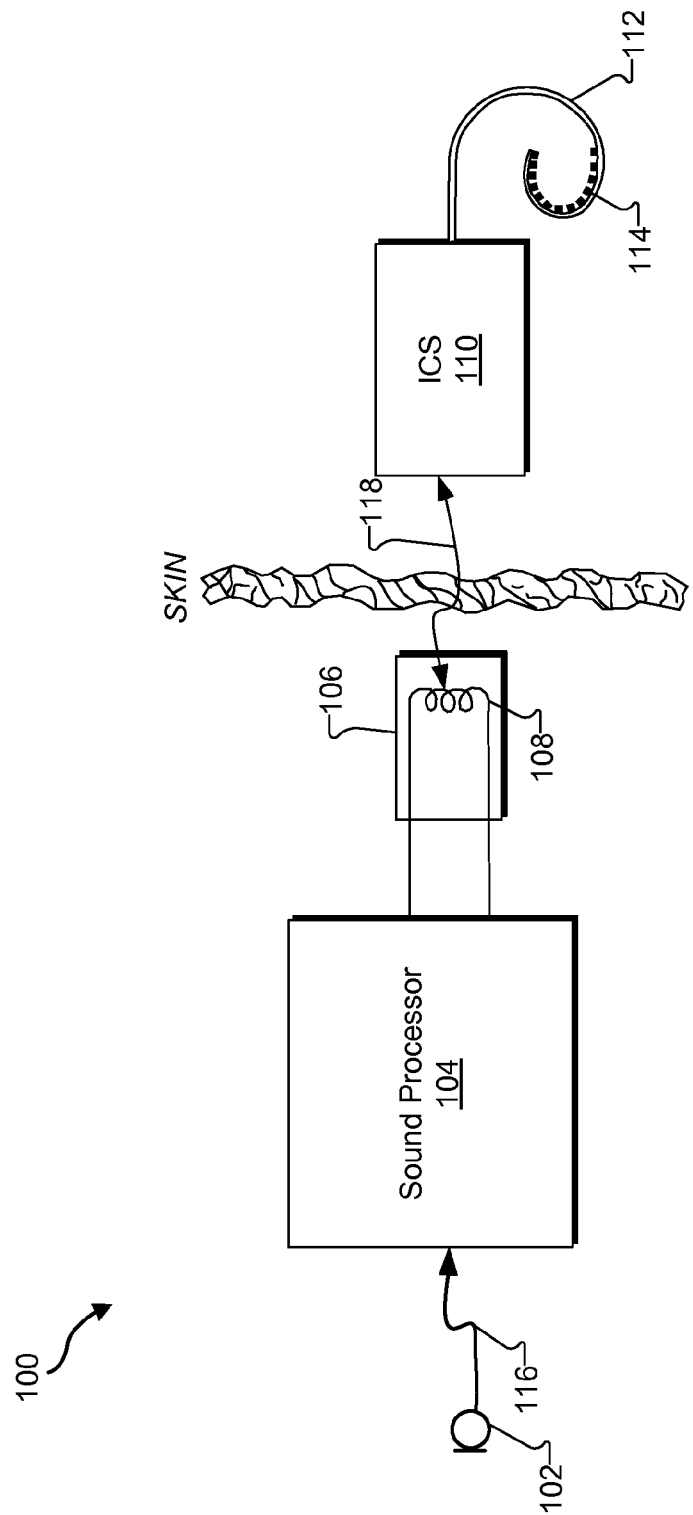
FIG. 1 illustrates an exemplary cochlear implant system according to principles described herein.

To facilitate an understanding of the methods and systems described herein, an exemplary cochlear implant system 100 will be described in connection with FIG. 1. As shown in FIG. 1, cochlear implant system 100 may include a microphone 102, a sound processor 104, a headpiece 106 having a coil 108 disposed therein, an implantable cochlear stimulator ("ICS") 110, and a lead 112 with a plurality of electrodes 114 disposed thereon. Additional or alternative components may be included within cochlear implant system 100 as may serve a particular implementation.

As shown in FIG. 1, microphone 102, sound processor 104, and headpiece 106 may be located external to a cochlear implant patient. In some alternative examples, microphone 102 and/or sound processor 104 may be implanted within the patient. In such configurations, the need for headpiece 106 may be obviated.

Microphone 102 may detect an audio signal and convert the detected signal to a corresponding electrical signal. The electrical signal may be sent from microphone 102 to sound processor 104 via a communication link 116, which may include a telemetry link, a wire, and/or any other suitable communication link.

Sound processor 104 is configured to direct implantable cochlear stimulator 110 to generate and apply electrical stimulation (also referred to herein as "stimulation current") to one or more stimulation sites within a cochlea of the patient. To this end, sound processor 104 may process the audio signal detected by microphone 102 in accordance with a selected sound processing strategy to generate appropriate stimulation parameters for controlling implantable cochlear stimulator 110. Sound processor 104 may include or be implemented by a behind-the-ear ("BTE") unit, a portable speech processor ("PSP"), and/or any other sound processing unit as may serve a particular implementation. Exemplary components of sound processor 104 will be described in more detail below.

Sound processor 104 may be configured to transcutaneously transmit one or more control parameters and/or one or more power signals to implantable cochlear stimulator 110 with coil 108 by way of a communication link 118. These control parameters may be configured to specify one or more stimulation parameters, operating parameters, and/or any other parameter by which implantable cochlear stimulator 110 is to operate as may serve a particular implementation. Exemplary control parameters include, but are not limited to, stimulation current levels, volume control parameters, program selection parameters, operational state parameters (e.g., parameters that turn a sound processor and/or an implantable cochlear stimulator on or off), audio input source selection parameters, fitting parameters, noise reduction parameters, microphone sensitivity parameters, microphone direction parameters, pitch parameters, timbre parameters, sound quality parameters, most comfortable current levels ("M levels"), threshold current levels, channel acoustic gain parameters, front and backend dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters. Sound processor 104 may also be configured to operate in accordance with one or more of the control parameters.

As shown in FIG. 1, coil 108 may be housed within headpiece 106, which may be affixed to a patient's head and positioned such that coil 108 is communicatively coupled to a corresponding coil included within implantable cochlear stimulator 110. In this manner, control parameters and power signals may be wirelessly transmitted between sound processor 104 and implantable cochlear stimulator 110 via communication link 118. It will be understood that data communication link 118 may include a bi-directional communication link and/or one or more dedicated uni-directional communication links. In some alternative embodiments, sound processor 104 and implantable cochlear stimulator 110 may be directly connected with one or more wires or the like.

Implantable cochlear stimulator 110 may be configured to generate electrical stimulation representative of an audio signal detected by microphone 102 in accordance with one or more stimulation parameters transmitted thereto by sound processor 104. Implantable cochlear stimulator 110 may be further configured to apply the electrical stimulation to one or more stimulation sites within the cochlea via one or more electrodes 114 disposed along lead 112. In some examples, implantable cochlear stimulator 110 may include a plurality of independent current sources each associated with a channel defined by one or more of electrodes 114. In this manner, different stimulation current levels may be applied to multiple stimulation sites simultaneously by way of multiple electrodes 114. In such examples, cochlear implant system 100 may be referred to as a "multi-channel cochlear implant system."

To facilitate application of the electrical stimulation generated by implantable cochlear stimulator 110, lead 112 may be inserted within a duct of the cochlea such that electrodes 114 are in communication with one or more stimulation sites within the cochlea. As used herein, the term "in communication with" refers to electrodes 114 being adjacent to, in the general vicinity of, in close proximity to, directly next to, or directly on the stimulation site. Any number of electrodes 114 (e.g., sixteen) may be disposed on lead 112 as may serve a particular implementation.

Figure 2:
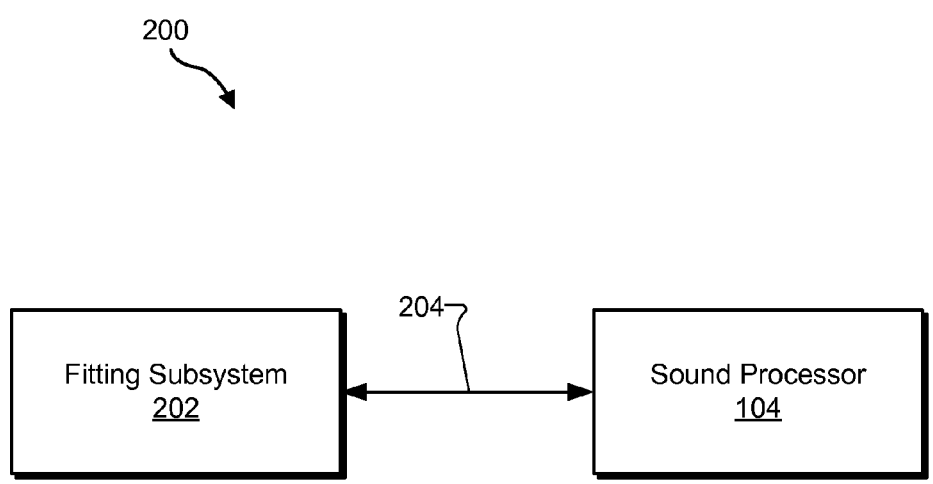
FIG. 2 illustrates an exemplary cochlear implant fitting system according to principles described herein.

FIG. 2 illustrates an exemplary cochlear implant fitting system 200 (or simply "fitting system 200") that may be used to fit sound processor 104 to a patient. As used herein, the terms "fitting a sound processor to a patient" and "fitting a cochlear implant system to a patient" will be used interchangeably to refer to performing one or more fitting operations associated with sound processor 104 and/or any other component of cochlear implant system 100. Such fitting operations may include, but are not limited to, adjusting one or more control parameters by which sound processor 104 and/or implantable cochlear stimulator 110 operate, measuring one or more electrode impedances, performing one or more neural response detection operations, and/or performing one or more diagnostics procedures associated with the cochlear implant system.

As shown in FIG. 2, fitting system 200 may include a fitting subsystem 202 configured to be selectively and communicatively coupled to sound processor 104 of cochlear implant system 100 by way of a communication link 204. Fitting subsystem 202 and sound processor 104 may communicate using any suitable communication technologies, devices, networks, media, and protocols supportive of data communications.

Fitting subsystem 202 may be configured to perform one or more of the fitting operations described herein. To this end, fitting subsystem 202 may be implemented by any suitable combination of computing and communication devices including, but not limited to, a fitting station, a personal computer, a laptop computer, a handheld device, a mobile device (e.g., a mobile phone), a clinician's programming interface ("CPI") device, and/or any other suitable component as may serve a particular implementation. An exemplary implementation of fitting subsystem 202 will be described in more detail below.

Figure 3:
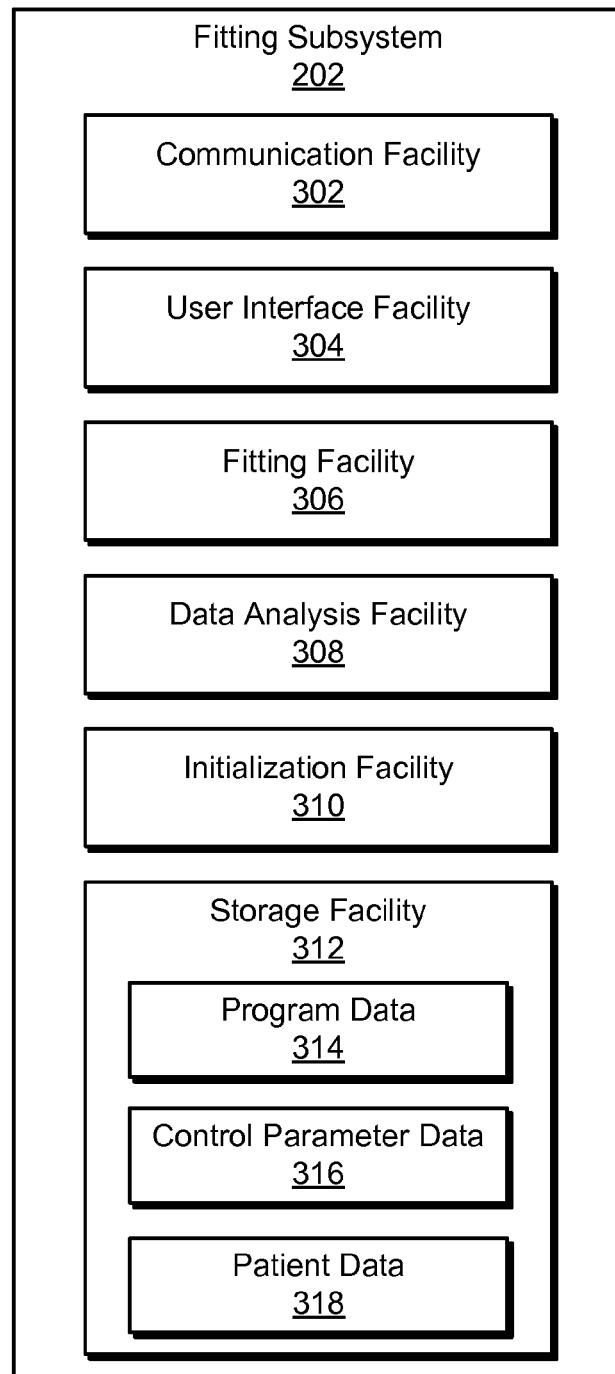
FIG. 3 illustrates exemplary components of an exemplary fitting subsystem according to principles described herein.

FIG. 3 illustrates exemplary components of fitting subsystem 202. As shown in FIG. 3, fitting subsystem 202 may include a communication facility 302, a user interface facility 304, a fitting facility 306, a data analysis facility 308, an initialization facility 310, and a storage facility 312, which may be communicatively coupled to one another using any suitable communication technologies. Each of these facilities will now be described in more detail.

Communication facility 302 may be configured to facilitate communication between fitting subsystem 202 and sound processor 104. For example, communication facility 302 may be implemented by a CPI device, which may include any suitable combination of components configured to allow fitting subsystem 202 to interface and communicate with sound processor 104. Communication facility 302 may additionally or alternatively include one or more transceiver components configured to wirelessly transmit data (e.g., program data and/or control parameter data) to sound processor 104 and/or wirelessly receive data (e.g., feedback data, impedance measurement data, neural response data, etc.) from sound processor 104.

Communication facility 302 may additionally or alternatively be configured to facilitate communication between fitting subsystem 302 and one or more other devices. For example, communication facility 302 may be configured to facilitate communication between fitting subsystem 302 and one or more computing devices (e.g., by way of the Internet and/or one or more other types of networks), reference implants, and/or any other computing device as may serve a particular implementation.

User interface facility 304 may be configured to provide one or more user interfaces configured to facilitate user interaction with fitting subsystem 202. For example, user interface facility 304 may provide a graphical user interface ("GUI") through which one or more functions, options, features, and/or tools associated with one or more fitting operations described herein may be provided to a user and through which user input may be received. In certain embodiments, user interface facility 304 may be configured to provide the GUI to a display device (e.g., a computer monitor) for display.

Fitting facility 306 may be configured to perform one or more of the fitting operations described herein. For example, fitting facility 306 may be configured to adjust one or more control parameters by which sound processor 104 and/or implantable cochlear stimulator 110 operate, direct sound processor 104 to measure one or more electrode impedances, perform one or more neural response detection operations, and/or perform one or more diagnostics procedures associated with cochlear implant system 100.

Fitting facility 306 may be configured to selectively use one or more sound processing programs that have been preloaded onto sound processor 104 to fit sound processor 104 to a patient. As used herein, the term "sound processing program" refers to any program that is executable by a sound processor included in a cochlear implant system. Hence, a sound processing program may specify a particular mode in which the sound processor is to operate. For example, a sound processing program may define a set of control parameters selected to optimize a listening experience of a cochlear implant patient in a particular listening environment (e.g., a relatively quiet room, a noisy restaurant, a musical environment, etc.). Other sound processing programs may be configured to facilitate measurement of one or more electrode impedances, performance of one or more neural response detection operations, and/or performance of one or more diagnostics procedures associated with the cochlear implant system. Loading and/or pre-loading of the one or more sound processing programs onto sound processor 104 may be performed in any suitable manner as may serve a particular implementation.

In some examples, fitting facility 306 may be configured to detect a condition prompting an initialization of a sound processor for a cochlear implant patient. For example, fitting facility 306 may detect a coupling of sound processor 104 that has not been previously associated with a patient or that is to be associated with a new patient to fitting subsystem 202. Additionally or alternatively, fitting facility 306 may detect user input representative of a request to initialize sound processor 104 and/or any other condition requiring initialization of sound processor 104.

Data analysis facility 308 may be configured to analyze data stored by sound processor 104 in response to fitting facility 306 detecting a condition prompting an initialization of sound processor 104. In some examples, the data analysis may be configured to verify an integrity of program data representative of one or more sound processing programs stored by sound processor 104. For example, data analysis facility 308 may be configured to determine whether the one or more sound processing programs represented by the program data are valid (i.e., properly functioning) and up-to-date (i.e., that there are not any newer versions of the one or more sound processing programs available for downloading to sound processor 104). Additionally or alternatively, data analysis facility 308 may be configured to determine whether sound processor 104 is correctly formatted with current system monitor and file system elements. In other words, data analysis facility 308 may determine whether sound processor 104 is properly formatted to include valid file system data, boot data, and/or any other type of system data.

Initialization facility 310 may be configured to perform one or more initialization procedures on sound processor 104. Such initialization procedures may include, but are not limited to, preparing sound processor 104 for fitting to a particular patient, associating sound processor 104 with a particular patient, associating sound processor 104 with no particular patient, associating sound processor 104 with a particular implantable cochlear stimulator 110, loading data onto sound processor 104, clearing data from sound processor 104, and/or otherwise preparing sound processor 104 for a fitting session in which sound processor 104 is to be fitted to a patient.

In some examples, initialization facility 310 may be configured to perform a "quick initialization" (also referred to as a "quick format") of sound processor 104 wherein header information stored by sound processor 104 is selectively rewritten to associate sound processor 104 with a patient. As used herein, "header information" refers to one or more data fields defined within a memory unit of sound processor 104 in which data identifying a patient associated with sound processor 104 may be written. In this manner, sound processor 104 may be assigned to the patient. Header information may additionally or alternatively include any other patient-specific data as may serve a particular implementation.

The quick initialization may additionally or alternatively include rewriting control data stored by sound processor 104 and representative of one or more control parameters associated with one or more sound processing programs stored by sound processor 104 with default control patient data representative of one or more default control parameters associated with the one or more sound processing programs. The default control parameters may be subsequently customized to the patient during a fitting procedure performed by fitting facility 306.

The quick initialization may additionally or alternatively include deleting one or more slots associated with one or more sound processing programs. As used herein, a "slot" is a logical concept associating a sound processing program and a set of control parameters with one of a plurality of program positions selectable via a hardware switch disposed on a sound processor (e.g., sound processor 104). When a specific slot is selected, the sound processor locates the sound processing program for that slot, begins executing the located sound processing program, and points the executed sound processing program at the set of control parameters that are also associated with that slot. Hence, by deleting all slots have that have sound processing programs associated therewith, the sound processing programs may be disassociated with the program positions, thereby restoring the sound processor 104 to a default state.

The quick initialization may additionally or alternatively include clearing any other patient-specific data from sound processor 104. In this manner, data specific to a patient previously associated with sound processor 104 may be removed from sound processor 104 and replaced with data specific to the patient to whom sound processor 104 is to be fitted.

Additionally or alternatively, initialization facility 310 may be configured to perform a "full initialization" (also referred to as a "full format") of sound processor 104 wherein the header information is selectively rewritten to associate sound processor 104 with a patient and wherein program data stored by sound processor 104 is rewritten with updated program data. The updated program data may be representative of a valid and up-to-date version of one or more sound processing programs. In some examples, a full initialization may further include clearing data stored by sound processor 104, writing any required boot and monitor information that is executed when sound processor 104 is turned on, creating an empty program library to which updated program data may be written, creating an empty global string library, creating an empty slot information library, creating directory information used to locate one or more elements of the file system, building one or more file allocation tables, and/or performing any other initialization procedure.

Initialization facility 310 may be configured to determine, based on the analysis performed by data analysis facility 308, which type of initialization (i.e., select between a quick initialization and a full initialization) to perform. For example, if data analysis facility 308 determines that the program data stored by sound processor is valid and up-to-date and that sound processor 104 is correctly formatted with current system monitor and file system elements, initialization facility 310 may perform a quick initialization of sound processor 104. Alternatively, if data analysis facility 308 determines that the program data stored by sound processor 104 is not valid or up-to-date, or if sound processor 104 is not correctly formatted with current system monitor and file system elements, initialization facility 310 may perform a full initialization of sound processor 104.

Storage facility 312 may be configured to maintain program data 314 representative of one or more sound processing programs, control parameter data 316 representative of one or more control parameters, and patient data 318 representative of data descriptive of or otherwise associated with one or more cochlear implant patients. Storage facility 312 may be configured to maintain additional or alternative data as may serve a particular implementation.

Figure 4:
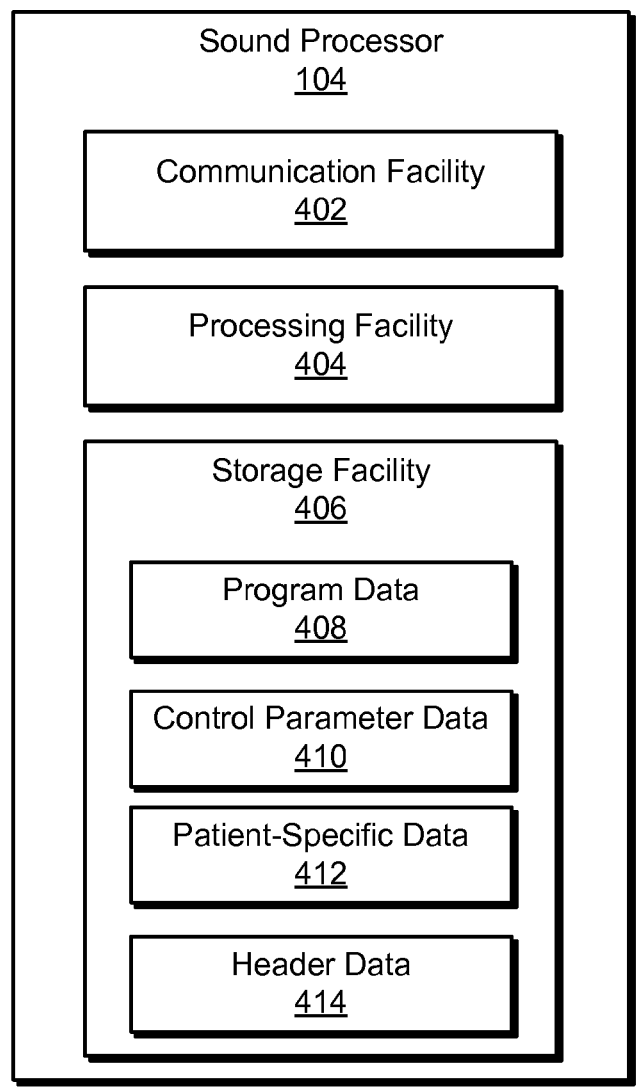
FIG. 4 illustrates exemplary components of a sound processor according to principles described herein.

FIG. 4 illustrates exemplary components of sound processor 104. As shown in FIG. 4, sound processor 104 may include a communication facility 402, a processing facility 404, and a storage facility 406, any or all of which may be in communication with one another using any suitable communication technologies. Each of these facilities will now be described in more detail.

Communication facility 402 may be configured to facilitate communication between sound processor 104 and fitting subsystem 202. For example, communication facility 402 may be configured to facilitate electrical coupling of sound processor 104 to a CPI device in order to communicate with fitting subsystem 202. Communication facility 402 may be further configured to facilitate communication between sound processor 104 and implantable cochlear stimulator 110. For example, communication facility 402 may include transceiver components configured to wirelessly transmit data (e.g., control parameters and/or power signals) to implantable cochlear stimulator 110 and/or wirelessly receive data from implantable cochlear stimulator 110.

Processing facility 404 may be configured to perform one or more signal processing heuristics on an audio signal presented to the patient. For example, processing facility 404 may perform one or more pre-processing operations, spectral analysis operations, noise reduction operations, mapping operations, and/or any other types of signal processing operations on a detected audio signal as may serve a particular implementation. In some examples, processing facility 404 may generate and/or adjust one or more control parameters governing an operation of implantable cochlear stimulator 110 (e.g., one or more stimulation parameters defining the electrical stimulation to be generated and applied by implantable cochlear stimulator 110). In some examples, processing facility 404 may be configured to operate in accordance with one or more sound processing programs stored within storage facility 406.

Storage facility 406 may be configured to maintain program data 408 representative of one or more sound processing programs, control parameter data 410 representative of one or more control parameters, patient-specific data 412 representative of data specific to a particular patient, and header data 414 configured to associate sound processor 104 with a particular patient. Storage facility 406 may be configured to maintain additional or alternative data as may serve a particular implementation.

Figure 5:
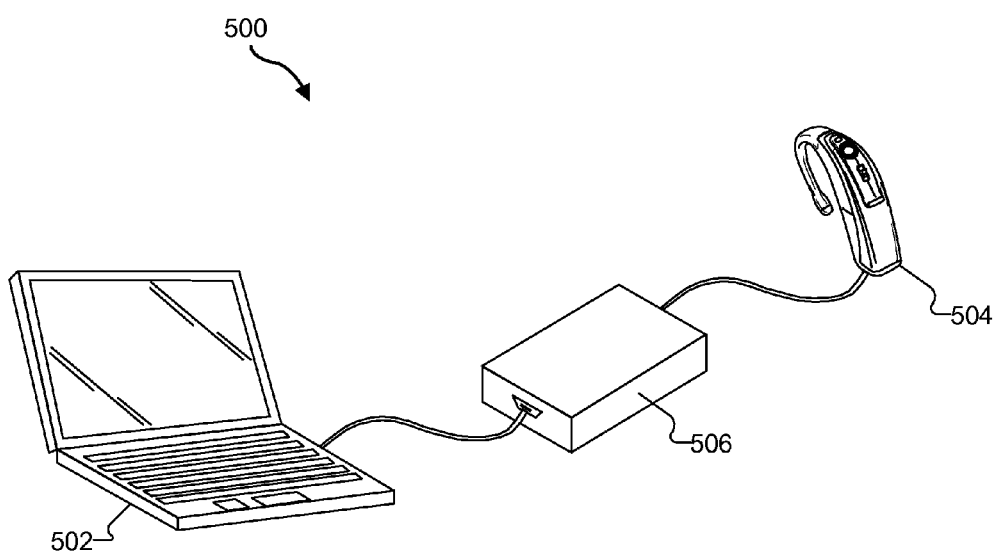
FIG. 5 illustrates an exemplary implementation of the cochlear implant fitting system of FIG. 2 according to principles described herein.

FIG. 5 illustrates an exemplary implementation 500 of fitting system 200. In implementation 500, a fitting station 502 may be selectively and communicatively coupled to a BTE unit 504 by way of a CPI device 506. BTE unit 504 is merely exemplary of the many different types of sound processors that may be used in accordance with the systems and methods described herein. Fitting station 502 may be selectively and communicatively coupled to any other type of sound processor as may serve a particular implementation.

Fitting station 502 may include any suitable computing device and/or combination of computing devices and be configured to perform one or more of the fitting operations described herein. For example, fitting station 502 may display one or more GUIs configured to facilitate pre-loading of one or more sound processing programs onto BTE unit 504, selection of one or more sound processing programs by which BTE unit 504 operates, adjustment of one or more control parameters by which BTE unit 504 operates, and/or any other fitting operation as may serve a particular implementation. Fitting station 502 may be utilized by an audiologist, a clinician, and/or any other user to fit BTE unit 504 to a patient.

CPI device 506 may be configured to facilitate communication between fitting station 502 and BTE unit 504. In some examples, CPI device 506 may be selectively and communicatively coupled to fitting station 502 and/or BTE unit 504 by way of one or more ports included within fitting station 502 and BTE unit 504.

Figure 6:
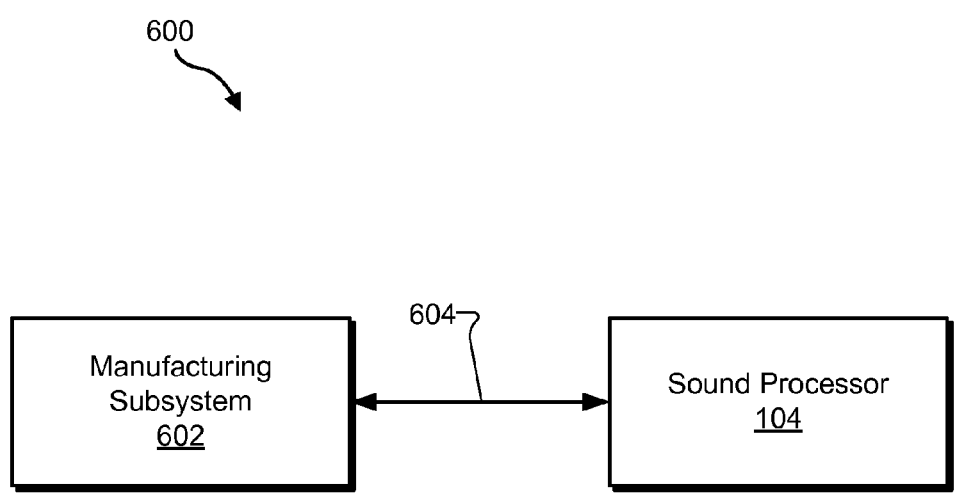
FIG. 6 shows an exemplary initialization system according to principles described herein.

As mentioned, program data representative of one or more sound processing programs may be pre-loaded onto sound processor 104. In some examples, the pre-loading may be included as part of a partial initialization of sound processor 104 performed by a manufacturing subsystem. To illustrate, FIG. 6 shows an exemplary initialization system 600 wherein a manufacturing subsystem 602 may be selectively and communicatively coupled to sound processor 104 by way of communication link 604. Manufacturing subsystem 602 and sound processor 104 may communicate using any suitable communication technologies, devices, networks, media, and protocols supportive of data communications.

Manufacturing subsystem 602 may be configured to perform a portion of a full initialization of sound processor 104. For example, manufacturing subsystem 602 may clear data stored by in sound processor 104, write any required boot and monitor information that is executed when sound processor 104 is turned on, create an empty program library to which program data may be written, create an empty global string library, create an empty slot information library, create directory information used to locate one or more elements of the file system, build one or more file allocation tables, load program data representative of one or more sound processing programs onto sound processor 104, and/or perform any other initialization procedure. In this manner, fitting subsystem 202 may simply complete the initialization process (e.g., by selectively rewriting header information stored by sound processor 104 to associate sound processor 104 with a particular patient). Such completion of the initialization process may be relatively fast (e.g., a few seconds) compared to the time it takes (e.g., several minutes) to perform a full initialization of sound processor 104.

In some examples, the partial initialization performed by manufacturing subsystem 602 may be specific to the particular type of sound processor 104. For example, with certain types of sound processors 104, the partial initialization may include clearing directory sectors included in a memory unit of sound processor 104, writing system monitor code that is executed when sound processor 104 is turned on, writing all remaining sectors except for the top two sectors as a linked list of free sectors, writing a program library directory sector with no entries, writing a file system directory sector indicating that all program slots are empty and including pointers to a list of free sectors and global string sectors, writing string sectors with appropriate data, and/or loading program data representative of one or more sound processing programs onto sound processor 104.

Alternatively, with certain other types of sound processors 104, the partial initialization performed by manufacturing subsystem 602 may include erasing all persistent memory (e.g., FLASH memory), writing boot loader code to the lowest four sectors, writing system monitor code, writing file system directory data (which may include, but is not limited to, allocation files, data representative of an initial empty program library directory, data representative of an initial empty slot directory, data representative of an initial empty set of global strings, data representative of an initial file system information sector used to locate various system directory related items, and/or one or more initial file allocation tables used to load files once they are located), writing string descriptors, and/or loading program data representative of one or more sound processing programs onto sound processor 104.

As mentioned, manufacturing subsystem 602 may be configured to load data representative of multiple sound processing programs onto sound processor 104 for use by sound processor 104 during and/or after a fitting session. In this manner, a user (e.g., an audiologist) of fitting subsystem 202 may direct sound processor 104 to switch between multiple sound processing programs during a fitting session in substantially real-time without having to wait for each sound processing program to be individually loaded onto sound processor 104 each time it is to be executed by sound processor 104.

In some examples, manufacturing subsystem 602 may be configured to pre-load program data representative of a plurality of sound processing programs onto sound processor 104 by transmitting the program data to sound processor 104 and directing sound processor to cache the program data as a library of sound processing programs in a memory unit included within sound processor 104. The program data may include any type of data (e.g., digital signal processing ("DSP") code) and may be cached within sound processor 104 for any amount of time as may serve a particular implementation.

In some examples, manufacturing subsystem 602 may be implemented by one or more computing devices located at a site associated with a manufacturer of sound processor 104 (e.g., a factory of the manufacturer and/or a factory of a third-party entity contracted or otherwise associated with the manufacturer). In this manner, the pre-loading of the program data may be performed by the manufacturer before sound processor 104 is delivered to the patient.

Figure 7:
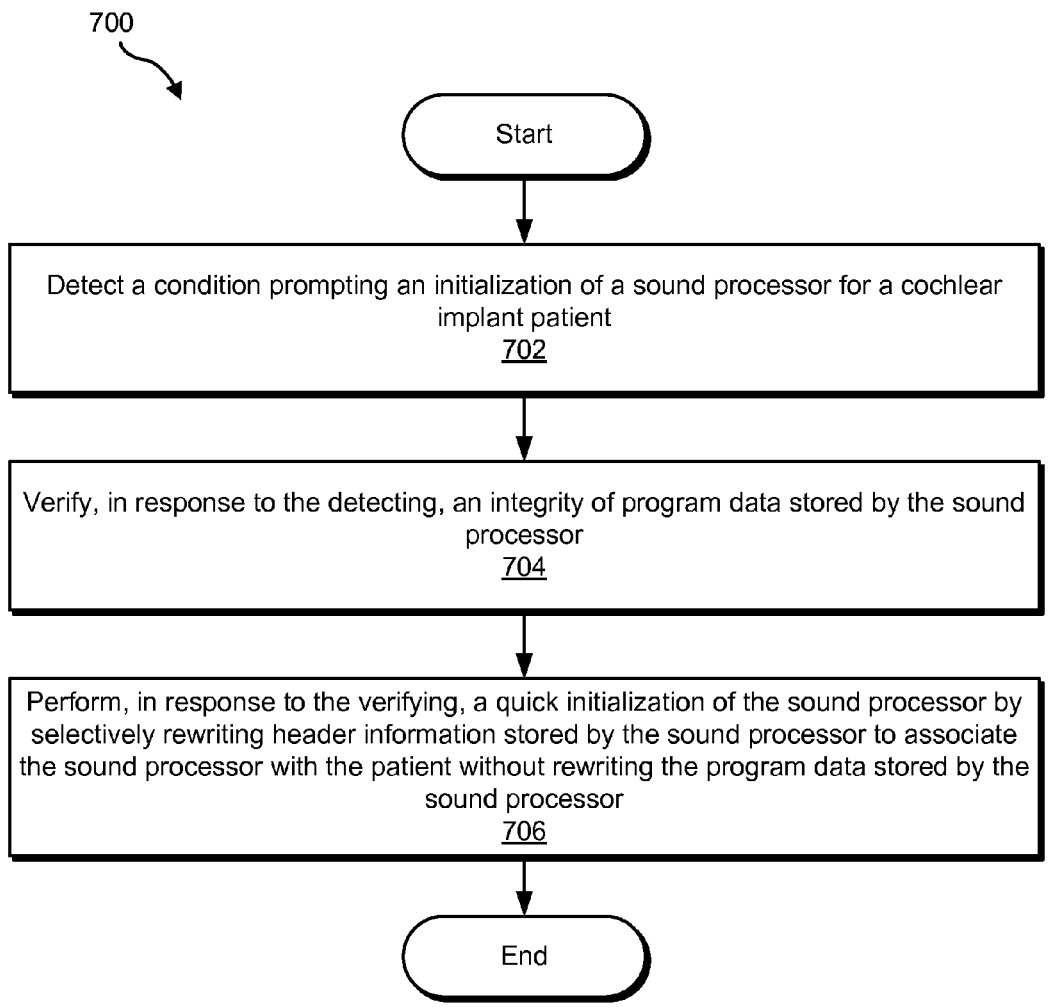
FIG. 7 illustrates an exemplary method of initializing a sound processor according to principles described herein.

FIG. 7 illustrates an exemplary method 700 of initializing a sound processor. While FIG. 7 illustrates exemplary steps according to one embodiment, other embodiments may omit, add to, reorder, and/or modify any of the steps shown in FIG. 7. One or more of the steps shown in FIG. 7 may be performed by any component or combination of components of fitting subsystem 202 and/or fitting station 502.

In step 702, a condition prompting an initialization of a sound processor for a cochlear implant patient is detected. The condition may be detected in any of the ways described herein. For example, step 702 may be performed by detecting a coupling of a sound processor that has not been previously associated with a patient or that is to be associated with a new patient to fitting subsystem 202. Additionally or alternatively, step 702 may be performed by detecting user input (e.g., by way of a graphical user interface) representative of a request to initialize a sound processor.

In step 704, in response to the detecting of the condition prompting the initialization of the sound processor, an integrity of program data stored by the sound processor may be verified. For example, step 704 may be performed by analyzing the program data stored by sound processor 104 to verify that the one or more sound processing programs represented by the program data are valid and up-to-date. Additionally or alternatively, step 704 may be performed by verifying that sound processor 104 is correctly formatted with current system monitor and file system elements.

In step 706, in response to the verifying performed in 704, a quick initialization of the sound processor may be performed by selectively rewriting header information stored by the sound processor to associate the sound processor with the patient without rewriting the program data stored by the sound processor. Step 706 may be performed in any suitable manner as may serve a particular implementation.

The quick initialization performed in step 706 may further include rewriting control parameter data with default control parameter data, deleting one or more slots associated with one or more sound processing programs, and/or clearing any other patient-specific data from the sound processor as described above.

In some examples, the quick initialization performed in step 706 may be performed automatically and transparently to a user of fitting subsystem 202. In this manner, an audiologist may simply connect a sound processor to fitting subsystem 202 and begin a fitting procedure without worrying about manually initializing the sound processor. Because the quick initialization is relatively fast (e.g., a few seconds or less), the sound processor may be initialized without causing the audiologist and/or patient to experience any significant delay associated with the initialization process.

Figure 8:
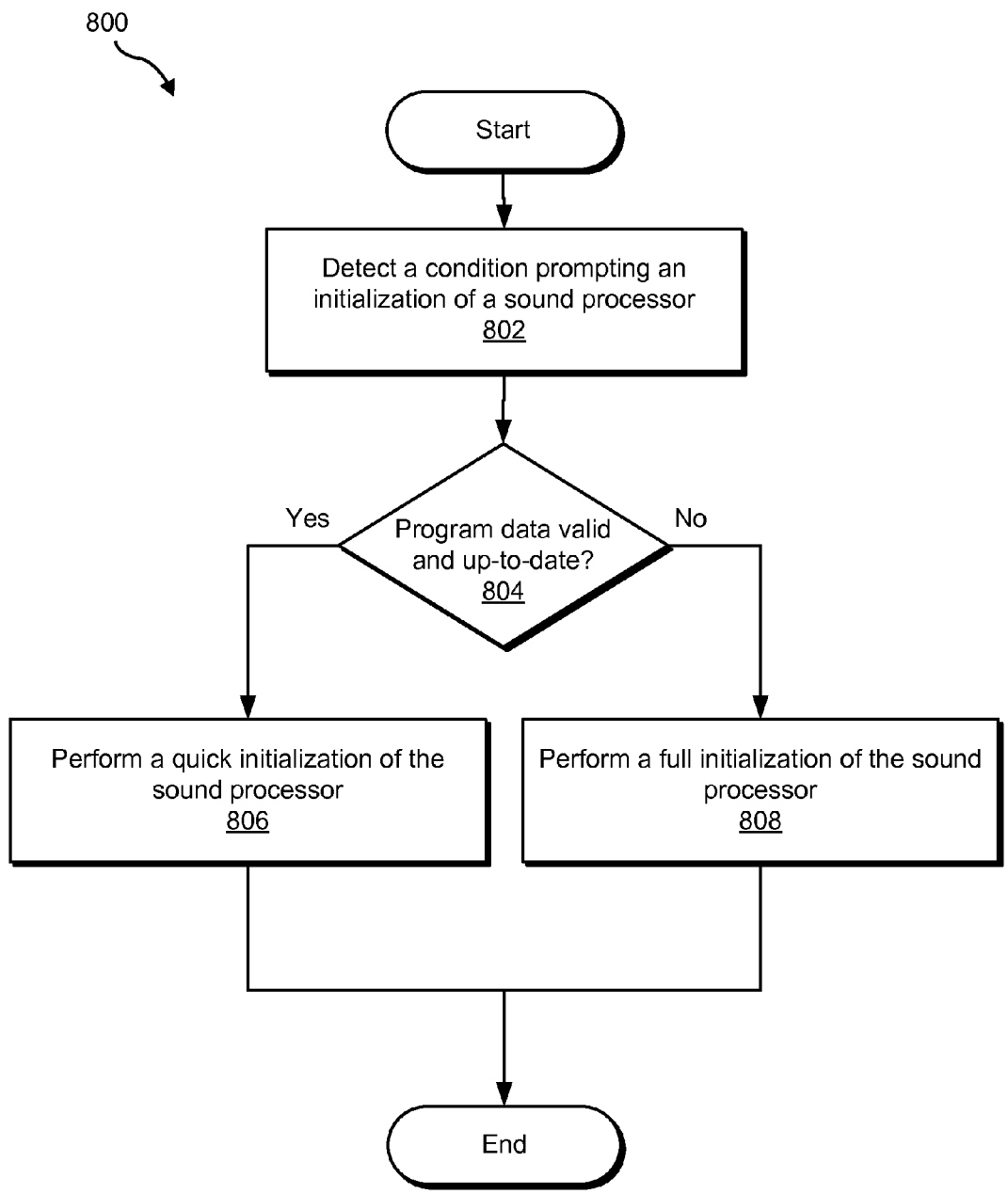
FIG. 8 illustrates another exemplary method of initializing a sound processor according to principles described herein.

FIG. 8 illustrates another exemplary method 800 of initializing a sound processor. While FIG. 8 illustrates exemplary steps according to one embodiment, other embodiments may omit, add to, reorder, and/or modify any of the steps shown in FIG. 8. One or more of the steps shown in FIG. 8 may be performed by any component or combination of components of fitting subsystem 202 and/or fitting station 502.

In step 802, a condition prompting an initialization of a sound processor is detected. The condition may be detected in any of the ways described herein. In some examples, the condition may indicate that the sound processor is to be initialized for a particular cochlear implant patient. Alternatively, the condition may indicate that the sound processor is to be initialized with no specific patient information.

In step 804, a determination is made whether program data stored by the sound processor and representative of one or more sound processing programs is valid and up-to-date. The determination may be made in any of the ways described herein.

In step 806, if it is determined that the program data is valid and up-to-date (Yes; step 804), a quick initialization of the sound processor is performed. The quick initialization may include selectively rewriting header information stored by the sound processor to associate the sound processor with a cochlear implant patient without rewriting the program data stored by the sound processor, rewriting control parameter data with default control parameter data, deleting one or more slots associated with one or more sound processing programs, and/or clearing any other patient-specific data from the sound processor as described above.

In step 808, if it is determined that the program data is not valid or up-to-date (No; step 804), a full initialization of the sound processor is performed. The full initialization may include any of the initialization steps described herein.

In some examples, if program data representative of multiple sound processing programs is stored by sound processor 104, the full initialization may include rewriting program data representative of only those sound processing programs that are determined to be invalid or out-of-date. In this manner, the entire program library does not have to be rewritten during a full initialization.

In certain embodiments, one or more of the components and/or processes described herein may be implemented and/or performed by one or more appropriately configured computing devices. To this end, one or more of the systems and/or components described above may include or be implemented by any computer hardware and/or computer-implemented instructions (e.g., software) embodied on a non-transitory computer-readable medium configured to perform one or more of the processes described herein. In particular, system components may be implemented on one physical computing device or may be implemented on more than one physical computing device. Accordingly, system components may include any number of computing devices, and may employ any of a number of computer operating systems.

In certain embodiments, one or more of the processes described herein may be implemented at least in part as instructions executable by one or more computing devices. In general, a processor (e.g., a microprocessor) receives instructions, from a tangible computer-readable medium, (e.g., a memory, etc.), and executes those instructions, thereby performing one or more processes, including one or more of the processes described herein. Such instructions may be stored and/or transmitted using any of a variety of known non-transitory computer-readable media.

A non-transitory computer-readable medium (also referred to as a processor-readable medium) includes any non-transitory medium that participates in providing data (e.g., instructions) that may be read by a computer (e.g., by a processor of a computer). Such a non-transitory medium may take many forms, including, but not limited to, non-volatile media and/or volatile media. Non-volatile media may include, for example, optical or magnetic disks and other persistent memory. Volatile media may include, for example, dynamic random access memory ("DRAM"), which typically constitutes a main memory. Common forms of non-transitory computer-readable media include, for example, a floppy disk, flexible disk, hard disk, magnetic tape, any other magnetic medium, a CD-ROM, DVD, any other optical medium, a RAM, a PROM, an EPROM, a FLASH-EEPROM, any other memory chip or cartridge, or any other non-transitory medium from which a computer can read.

Figure 9:
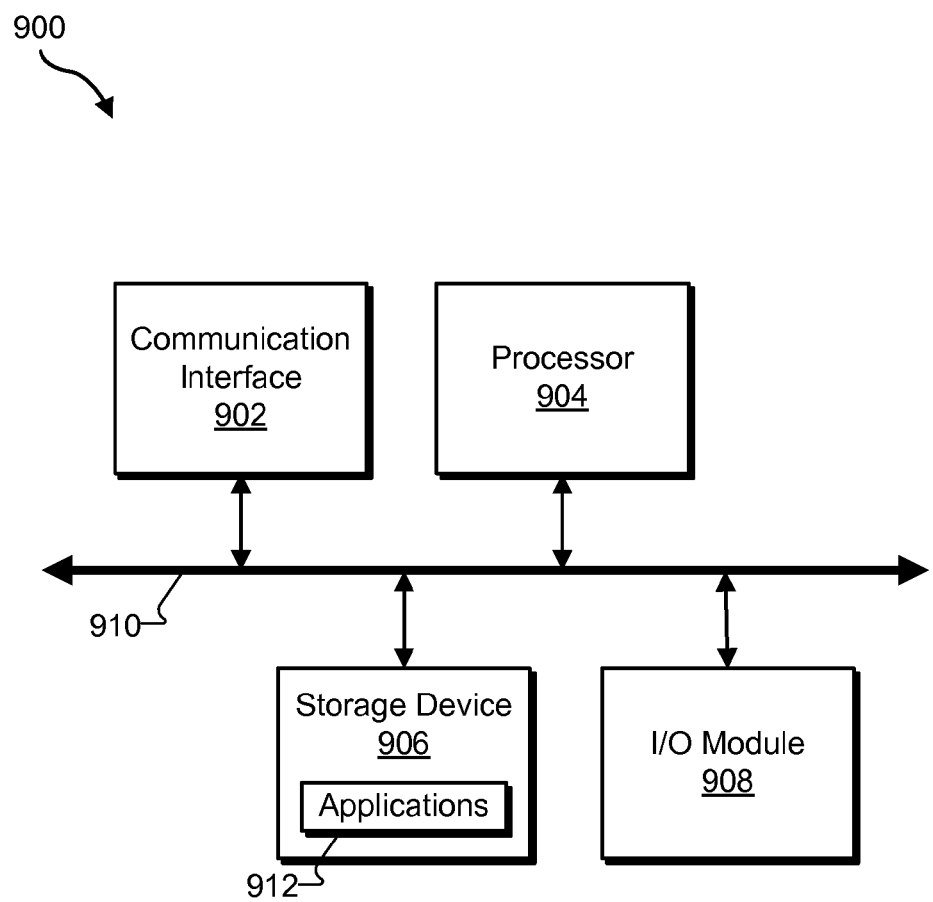
FIG. 9 illustrates an exemplary computing device according to principles described herein.

FIG. 9 illustrates an exemplary computing device 900 that may be configured to perform one or more of the processes described herein. As shown in FIG. 9, computing device 900 may include a communication interface 902, a processor 904, a storage device 906, and an input/output ("I/O") module 908 communicatively connected via a communication infrastructure 910. While an exemplary computing device 900 is shown in FIG. 9, the components illustrated in FIG. 9 are not intended to be limiting. Additional or alternative components may be used in other embodiments. Components of computing device 900 shown in FIG. 9 will now be described in additional detail.

Communication interface 902 may be configured to communicate with one or more computing devices. Examples of communication interface 902 include, without limitation, a wired network interface (such as a network interface card), a wireless network interface (such as a wireless network interface card), a modem, and any other suitable interface. Communication interface 902 may additionally or alternatively provide such a connection through, for example, a local area network (such as an Ethernet network), a personal area network, a telephone or cable network, a satellite data connection, a dedicated URL, or any other suitable connection. Communication interface 902 may be configured to interface with any suitable communication media, protocols, and formats, including any of those mentioned above.

Processor 904 generally represents any type or form of processing unit capable of processing data or interpreting, executing, and/or directing execution of one or more of the instructions, processes, and/or operations described herein. Processor 904 may direct execution of operations in accordance with one or more applications 912 or other computer-executable instructions such as may be stored in storage device 906 or another non-transitory computer-readable medium.

Storage device 906 may include one or more data storage media, devices, or configurations and may employ any type, form, and combination of data storage media and/or device. For example, storage device 906 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 906. For example, data representative of one or more executable applications 912 (which may include, but are not limited to, one or more of the software applications described herein) configured to direct processor 904 to perform any of the operations described herein may be stored within storage device 906. In some examples, data may be arranged in one or more databases residing within storage device 906.

I/O module 908 may be configured to receive user input and provide user output and may include any hardware, firmware, software, or combination thereof supportive of input and output capabilities. For example, I/O module 908 may include hardware and/or software for capturing user input, including, but not limited to, a keyboard or keypad, a touch screen component (e.g., touch screen display), a receiver (e.g., an RF or infrared receiver), and/or one or more input buttons.

I/O module 908 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 908 is configured to provide graphical data to a display for presentation to a user. The graphical data may be representative of one or more graphical user interfaces and/or any other graphical content as may serve a particular implementation.

In some examples, any of the facilities and/or subsystems described herein may be implemented by or within one or more components of computing device 900. For example, one or more applications 912 residing within storage device 906 may be configured to direct processor 904 to perform one or more processes or functions associated with communication facility 302, user interface facility 304, fitting facility 306, data analysis facility 308, initialization facility 310, communication facility 402, processing facility 404, and/or manufacturing subsystem 602. Likewise, storage facility 312 and/or storage facility 406 may be implemented by or within storage device 906.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:
    detecting, by a fitting subsystem, a condition prompting an initialization of a sound processor for a cochlear implant patient;
    verifying, by the fitting subsystem in response to the detecting, an integrity of program data stored by the sound processor, the program data representative of one or more sound processing programs; and
    performing, by the fitting subsystem in response to the verifying, a quick initialization of the sound processor by selectively rewriting header information stored by the sound processor to associate the sound processor with the patient without rewriting the program data stored by the sound processor.

2. The method of claim 1, wherein the performing of the quick initialization of the sound processor further comprises rewriting, by the fitting subsystem in response to the verifying, control parameter data stored by the sound processor and representative of one or more control parameters associated with the one or more sound processing programs with default control patient data representative of one or more default control parameters associated with the one or more sound processing programs.

3. The method of claim 1, wherein the performing of the quick initialization of the sound processor further comprises clearing, by the fitting subsystem in response to the verifying, patient-specific data from the sound processor, the patient-specific data specific to a patient previously associated with the sound processor.

4. The method of claim 1, wherein the performing of the quick initialization of the sound processor further comprises deleting one or more slots associated with the one or more sound processing programs.

5. The method of claim 1, wherein the verifying further comprises verifying that the sound processor is correctly formatted with current system monitor and file system elements.

6. The method of claim 1, wherein the verifying of the integrity of the program data comprises verifying that the program data is valid and up-to-date.

7. The method of claim 1, wherein the detecting of the condition prompting the initialization comprises detecting user input representative of a request to initialize the sound processor.

8. The method of claim 1, wherein the detecting of the condition prompting the initialization comprises detecting a coupling of the sound processor to a computing device utilized by an audiologist to fit the sound processor to the patient.

9. The method of claim 1, wherein the quick initialization is performed automatically and transparently to a user of the fitting subsystem.

10. The method of claim 1, further comprising performing, by a manufacturing subsystem prior to the quick initialization, a portion of the initialization of the sound processor.

11. The method of claim 10, wherein the performing of at least a portion of the initialization of the sound processor comprises pre-loading the program data onto the sound processor.

12. The method of claim 1, embodied as computer-executable instructions on at least one non-transitory computer-readable medium.

13. A method comprising:
   detecting, by a fitting subsystem, a condition prompting an initialization of a sound processor;
   determining, by the fitting subsystem in response to the detecting, whether program data stored by the sound processor and representative of one or more sound processing programs is valid and up-to-date;
   performing, by the fitting subsystem if the program data is valid and up-to-date, a quick initialization of the sound processor; and
   performing, by the fitting subsystem if the program data is not valid or up-to-date, a full initialization of the sound processor.

14. The method of claim 13, wherein the performing of the quick initialization comprises selectively overwriting header information stored by the sound processor to associate the sound processor with a cochlear implant patient.

15. The method of claim 13, wherein the performing of the quick initialization comprises rewriting control parameter data stored by the sound processor and representative of one or more control parameters associated with the one or more sound processing programs with default control patient data representative of one or more default control parameters associated with the one or more sound processing programs.

16. The method of claim 13, wherein the performing of the full initialization comprises rewriting the program data with updated program data representative of a valid and up-to-date version of the one or more sound processing programs.

17. The method of claim 13, wherein the detecting of the condition prompting the initialization comprises detecting a coupling of the sound processor to a computing device utilized by an audiologist to fit the sound processor to a cochlear implant patient.

18. The method of claim 13, embodied as computer-executable instructions on at least one non-transitory computer-readable medium.

19. A system comprising:
   a fitting facility that detects a condition prompting an initialization of a sound processor for a cochlear implant patient;
   a data analysis facility communicatively coupled to the fitting facility and that verifies an integrity of program data stored by the sound processor in response to the detection of the condition, the program data representative of one or more sound processing programs; and
   an initialization facility communicatively coupled to the data analysis facility and configured to perform a quick initialization of the sound processor in response to the verification of the integrity of the program data by selectively rewriting header information stored by the sound processor to associate the sound processor with the patient without rewriting the program data stored by the sound processor.

20. The system of claim 19, wherein the initialization facility is further configured to perform the quick initialization of the sound processor by clearing patient-specific data from the sound processor, the patient-specific data specific to a patient previously associated with the sound processor.

* * * * *